United States Patent [19]

Franz et al.

[11] Patent Number: 4,534,911

[45] Date of Patent: Aug. 13, 1985

[54] METHOD FOR THE PREPARATION OF P-BUTOXYPHENYLACETYL-HYDROXAMIC ACID IN THE FINELY DIVIDED STATE AND A COMPOSITION CONTAINING THIS ACID

[75] Inventors: Michel R. Franz, Berchem-Sainte-Agathe; Andreas B. Vincze, Woluwé-Saint-Lambert; Georges E. Lambelin, Forest, all of Belgium; Alain V. Polat, Onex-Geneve, Switzerland

[73] Assignee: Continental Pharma, Inc., Vadiz, Liechtenstein

[21] Appl. No.: 558,885

[22] Filed: Dec. 7, 1983

[30] Foreign Application Priority Data

Dec. 13, 1982 [LU] Luxembourg ............................ 84530

[51] Int. Cl.$^3$ ..................... C07C 83/10; A61K 31/185
[52] U.S. Cl. ............................. 514/575; 260/500.5 H
[58] Field of Search ................................. 260/500.5 H

[56] References Cited

FOREIGN PATENT DOCUMENTS

| 77646 | 5/1982 | Japan | 260/500.5 H |
|---|---|---|---|
| 921536 | 3/1963 | United Kingdom | 260/500.5 H |
| 390074 | 11/1973 | U.S.S.R. | 260/500.5 H |
| 632690 | 11/1978 | U.S.S.R. | 260/500.5 H |

OTHER PUBLICATIONS

Chemical Abstracts, vol. 96, No. 18, (1982), No. 149082t, p. 415.

*Primary Examiner*—J. E. Evans
*Attorney, Agent, or Firm*—Cushman, Darby & Cushman

[57] ABSTRACT

Method for the preparation of micronized p-butoxyphenylacetylhydroxamic acid, comprising dissolving the p-butoxyphenylacetylhydroxamic acid in a basic solution of salifying agent and then precipitating it in an acid solution in the presence of a surface-active agent.

10 Claims, No Drawings

METHOD FOR THE PREPARATION OF P-BUTOXYPHENYLACETYL-HYDROXAMIC ACID IN THE FINELY DIVIDED STATE AND A COMPOSITION CONTAINING THIS ACID

The present invention relates to a method for the preparation of p-butoxyphenylacetylhydroxamic acid in the finely divided state.

P-butoxyphenylacetylhydroxamic acid, known under the generic term of "Bufexamac", is a molecule with acknowledged anti-inflammatory activity, which corresponds to the following formula:

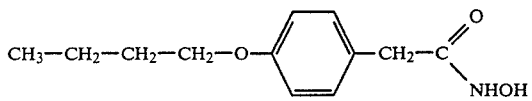

This molecule has very low solubility in water and its salts are not very stable.

Generally, in the case of a medicinal constituent having low water-solubility, it is important to have available a variety of starting material corresponding to a finely divided product now termed "micronised".

Moreover, the Noyes and Whitney equation, which governs the phenomenon of dissolution which the medicament should satisfy before being absorbed, indicates that the rate of dissolution is proportional to the area of the particles in contact with the physiological media.

The utilisation of a reduced particle size offering a large area is therefore a beneficial factor during the preparation of forms for oral use, such as tablets, capsules and soft capsules or of forms for topical or rectal use.

Then again, in the case of products having low water-solubility, the development of a plurality of galenical forms as suspensions starting from a finely divided substance, on a microscopic scale, is advantageous from various points of view: improved local tolerance in the case of injections or collyria and technological development of more convenient galenical forms, particularly in the case of injectable products.

The production of an anti-inflammatory product in the finely divided state, such as bufexamac, makes possible in particular the development of collyria and of injectable intra-articular forms in a therapeutic field in which the derivatives of cortisone are widely used; this represents an advance because cortisone derivatives exhibit side effects which are detrimental in respect of certain hormonal functions, the cicatrization process and immunological defence.

The physical methods of reducing the particles size (pulverising by means of a colloidal mill, compressed-air microniser or jet mill) do not lead to satisfactory results in the case of bufexamac; the starting crystals cannot be divided and the products obtained have a considerable percentage of decomposition.

Microcrystallisation techniques have been tested, without giving favourable results: controlled crystallisation, ultrasonic action, technique of successive dilution and reprecipitation, solvation and desolvation.

An essential object of the invention is to propose a method for the preparation of p-butoxyphenylacetylhydroxamic acid in the finely divided state, particularly in the form of microscopic particles, enabling the disadvantages of the above-mentioned known methods to be eliminated.

For this purpose, the method according to the invention lies in dissolving the p-butoxyphenylacetylhydroxamic acid in a solution of a salifying agent and then precipitating it in an acid solution in the presence of surface-active agent.

Advantageously, the method comprises dissolving the p-butoxyphenylacetylhydroxamic acid in a solution of an alkali metal base.

The invention also concerns a pharmaceutical composition obtained by carrying out the above-described method.

Further details and features of the invention will appear in the following description, given by way of non-restrictive example, of several forms of embodiment of the method according to the invention.

After many tests it was found, surprisingly, in accordance with the invention that the introduction of a not aqueous solution of a bufexamac salt into an aqueous acid solution containing a surfactant makes it possible to obtain a suspension of crystals which are of greatly reduced size, are chemically pure and physically stable.

The salification of the bufexamac is preferably effected by a sufficiently strong base which is pharmaceutically acceptable; the use of alkali metal salts is recommended. Preferentially, sodium hydroxide is used.

Very satisfactory results are obtained when the aqueous solution of salifying agent is previously heated to a temperature of between 40° and 75° C., or better still between 50° and 60° C. and ideally at 55° C.±3° C.

The amount of salifying agent used will advantageously be calculated in slight excess so as to dissolve the bufexamac in the shortest possible time.

The acid used to neutralise the salt formed extemporaneously may be organic or inorganic; it will have to be compatible with administration to man or to animal.

Among the acids which can be used it is possible to mention tartaric, aspartic, citric, phosphoric, sulphuric and hydrochloric acid.

The amount of acid introduced is calculated so as to neutralise the base and to liberate the finely divided bufexamac.

To prepare and preserve the bufexamac particles in finely divided form it is necessary to form an interfacial film between the particles and the ambient medium.

Preferably, this film should be achieved by means of a non-ionic surfactant only compatible, in particular, with administration by injection.

A surfactant is a substance having composite nature as a result of the existence therein of functional hydrophilic and lipophilic groups.

Bonds have to be able to be formed between the functional groups of the surfactant and the bufexamac.

The value of the hydrolipophilic balance is the fundamental characteristic of a nonionic surfactant; it represents the capacity of the surfactant to disperse a product in its medium.

This capacity is influenced by the polarity of the functional group (for example alcoholic hydroxyl, ethylene oxide, fatty acid), their nature, their structure, the degree of condensation, etc. . . .

The value of the hydrolipophilic balance (HLB) represents the ratio of hydrophilic tendencies (H) and lipophilic tendencies (L) of the molecule.

Artificially, the value 10 has been attributed to those surfactants in which the two types of group are in equilibrium.

After a plurality of tests, it has been found that an HLB value of between 10 and 18 was desirable for the preparation of finely divided bufexamac with a very high field.

To avoid any degradation phenomena, the preparation of the salt and the neutralisation by precipitation in the acid solution containing the surfactant should take place, advantageously, within a period of a few minutes.

The finely divided product can be isolated or prepared in the final medium of the formultation, without isolating the starting material.

The particle-size analysis of the bufexamac obtained was carried out using a Coulter Counter apparatus; the particle size corresponded satisfactorily to a finely divided product which remained stable during preservation, as the following table shows.

| | | Particle-size analysis. | | | |
|---|---|---|---|---|---|
| (1) Median number* (2) Median weight** (3) Maximum size found | | Batch 795/016 | | Batch 796/018 | |
| | | A | B | A | B |
| at the start | (1) | 1.88 | | 1.77 | |
| | (2) | 2.76 | | 1.98 | |
| | (3) | 19.32 | | 19.32 | |
| after 8 months | (1) | 1.85 | 1.84 | 1.87 | 1.88 |
| | (2) | 2.32 | 2.75 | 2.73 | 2.63 |
| | (3) | 19.32 | 19.32 | 19.32 | 12.17 |
| after 36 months | (1) | 2.09 | 2.13 | 1.88 | 2.09 |
| | (2) | 2.93 | 3.28 | 2.90 | 3.21 |
| | (3) | 19.32 | 15.33 | 19.32 | 15.33 |

*Median number: 50% of the particles (in number) have a diameter less than or equal to the figure mentioned.
**Median weight: 50% of the particles (by weight or volume) have a diameter less than or equal to the figure mentioned.

The Table indicates in microns the measurements effected on two batches of suspension preserved at normal temperature (columns A) and at a temperature of 35° C. (columns B).

The chemical stability of the finely divided product has likewise been demonstrated in the course of time, in particular using chromatographical methods.

The following examples are given to illustrate the invention without limiting it in any way.

EXAMPLE 1

Composition:

| | | | |
|---|---|---|---|
| a. | { | Bufexamac | 2000 g |
| | | sodium hydroxide | 360 g |
| | | demineralised water | 14300 ml |
| b. | { | crystallised citric acid | 1070 g |
| | | Tween 80 ® | 360 g |
| | | demineralised water | 36000 ml |

Mode of operation:
1. Prepare a solution of sodium hydroxide with the constituents a. Bring this solution to a temperature of between 55° and 58° C. Dissolve the bufexamac therein.
2. Prepare an acid solution of surfactant with the constituents b.
3. Pour the hot solution (55°–58° C.) of the sodium salt of bufexamac into the acid solution which is maintained, with agitation, at ambient temperature.
4. The precipitate obtained is filtered on paper and washed with distilled water until a neutral filtrate is obtained.
5. Drying.

EXAMPLE 2

Composition:

| | | | |
|---|---|---|---|
| a. | { | Bufexamac | 100 g |
| | | potassium hydroxide | 25.2 g |
| | | demineralised water | 715 ml |
| b. | { | hydrochloric acid | 17.7 g |
| | | Tween 60 ® | 20 g |
| | | demineralised water | 1800 ml |

Mode of operation:
1. Bring a solution of sodium hydroxide with the products a. to temperature of 55°–58° C.
2. Add the bufexamac.
3. Agitate until complete dissolution.
4. Prepare at ambient temperature an acid solution of surfactant with the products b.
5. Pour the alkaline solution of bufexamac maintained at 55°–58° C. into the acid solution.
6. The bufexamac obtained is filtered on paper and then washed with the demineralised water until complete neutrality of the filtrate.
7. Drying.

The products prepared according to Examples 1 and 2 can be used as starting material in the preparation of oral forms, such as tablets, capsules and soft capsules, and of forms for topical or rectal use.

Conventional excipients can be used in these formulations.

EXAMPLE 3

Composition:

| | | | |
|---|---|---|---|
| a. | { | Bufexamac | 20.6 g |
| | | sodium hydroxide | 3.725 g |
| | | twice distilled water | 250 ml |
| b. | { | hydrochloric acid 1 N | 97 ml |
| | | Tween 80 ® | 4 g |
| | | Twice distilled water | 200 ml |
| c. | { | carboxymethylcellulose (CMC) | 10 g |
| | | preserving agent | q.s. |
| | | NaCl | 3 g |
| | | twice distilled water q.s. to | 1000 ml |

Mode of operation:
1. Prepare a sodium solution with the constituents a. Filter this solution sterilely on a filter 0.22μ.
2. Prepare a solution of hydrochloric acid and Tween 80 with the constituents b. Filter this solution sterilely on a filter 0.22μ.
3. Prepare a solution with the constituents c. Filter on fritted glass no. 2. Sterilise at 120° C. for 20 minutes.
4. Bring the solution 1 to 55° C. and dissolve therein the previously screened bufexamac.
5. Pour the solution 4 into solution 2 while agitating vigorously.
6. Adjust the pH to a value of 6.5±0.5 using a dilute solution of sodium hydroxide.
7. Add solution 3 to the suspension.
8. Distribute in ampoules under aseptic conditions.

EXAMPLE 4

Composition:

|   |   | Bufexamac | 41.2 g |
|---|---|---|---|
| a. | { | sodium hydroxide | 7.45 g |
|   |   | twice distilled water | 500 ml |
| b. | { | hydrochloric acid 1 N | 194 ml |
|   |   | Tween 20 ® | 8.24 g |
|   |   | twice distilled water | 400 ml |
| c. |   | carboxymethylcellulose (CMC) | 20 g |
|   | { | benzyl alcohol | 20 g |
|   |   | NaCl | 6 g |
|   |   | twice distilled water q.s. to | 2000 ml |

Mode of operation:

1. Prepare a solution of sodium hydroxide using the constituents a. Filter this solution sterilely on a filter 0.22μ.
2. Prepare a solution of hydrochloric acid and Tween 20 using the constituents b. Filter this solution sterilely on a filter 0.22μ.
3. Dissolve the CMC and the NaCl in the twice distilled water indicated under c. Filter on fritted glass no. 2. Sterilise at 120° C. for 20 minutes. Then add the previously filtered benzyl alcohol.
4. Bring solution 1 to 55° C. and dissolve therein the screened bufexamac.
5. Pour solution 4 into solution 2.
6. Bring the pH to a value of 6.5±0.5 using a dilute solution of sodium hydroxide.
7. Add solution 3 to the suspension obtained in 6.
8. Distribute sterilely in sterile collyrium bottles.

In these Examples, the term "Tween" designates polyoxyethylenated esters of sorbitan marketed by the firm Atlas Chemical.

Of course, the invention is not limited to the forms of embodiment described and it is possible to envisage variants without departing from the scope of this patent.

For example therefore, a bufexamac salt could be introduced directly into the acid solution containing the surfactant.

We claim:

1. Method for the preparation of micronised p-butoxyphenylacetylhydroxamic acid, characterised in that it comprises dissolving the p-butoxyphenylacetylhydroxamic acid in a basic solution of salifying agent and then precipitating it in an acid solution in the presence of a surface-active agent the hydrolipophilic balance of which is between 10 and 18.

2. Method according to claim 1, which comprises adding the solution of salifying agent to the acid solution, while maintaining this latter solution under agitation.

3. Method according to claim 1, wherein a solution of salifying agent is used containing a relatively strong base.

4. Method according to claim 3, which comprises dissolving the p-butoxyphenylacetylhydroxamic acid in a solution of an alkali metal base.

5. Method according to claim 1, which comprises dissolving the p-butoxyphenylacetylhydroxamic acid in the solution of salifying agent at a temperature of between 40° and 75° C., advantageously between 50° and 60° C. and, preferably, at 55° C.±3° C.

6. Method according to claim 1, which comprises effecting the precipitation, at ambient temperature, in a solution of a pharmaceutically acceptable organic or mineral acid.

7. Method according to claim 1, comprising the use of a solution of salifying agent in slight excess in relation to the quantity of p-butoxyphenylacetylhydroxamic acid to be dissolved therein.

8. Method according to claim 1, comprising the use of, for the preparation of the p-butoxyphenylacetylhydroxamic acid, a solution of an acid chosen from the group formed by tartaric, aspartic, citric, phosphoric, sulphuric and hydrochloric acid.

9. Method according to claim 1, which comprises precipitating the p-butoxyphenylacetylhydroxamic acid by addition of a solution of sodium salt in a solution of hydrochloric acid provided at ambient temperature and containing a polyoxyethylenated ester of sorbitan.

10. Method according to claim 1, which comprises precipitating the p-butoxyphenylacetylhydroxamic acid in the presence of suitable excipients, without isolating the precipitated p-butoxyphenylacetylhydroxamic acid.

* * * * *